US005622581A

United States Patent [19]
Ducker et al.

[11] Patent Number: 5,622,581
[45] Date of Patent: Apr. 22, 1997

[54] DISPOSABLE GARMENT WITH DE-ELASTICIZED ELASTIC MEMBERS AND METHOD FOR MAKING SAME

[75] Inventors: Paul Ducker, Vancouver, Wash.; Adrian Wright, Canby, Oreg.; Walter V. Klemp, Houston, Tex.

[73] Assignee: Drypers Corporation, Houston, Tex.

[21] Appl. No.: 630,232

[22] Filed: Apr. 10, 1996

Related U.S. Application Data

[63] Continuation of Ser. No. 269,236, Jun. 30, 1994, abandoned.

[51] Int. Cl.⁶ .............................. A61F 13/15; A61F 13/20
[52] U.S. Cl. .......................... 156/163; 156/164; 156/229; 156/496; 604/358; 604/373; 604/385.2

[58] Field of Search .................................. 604/358, 369, 604/373, 385.1, 385.2; 156/160, 229, 496, 163, 164

[56] References Cited

U.S. PATENT DOCUMENTS

| | | |
|---|---|---|
| 4,450,026 | 5/1984 | Pienak et al. . |
| 4,895,568 | 1/1990 | Enloe .................................. 604/385.1 |
| 5,055,103 | 10/1991 | Nomura et al. ...................... 604/385.2 |

Primary Examiner—P. Zuttarelli
Attorney, Agent, or Firm—Fulbright & Jaworski

[57] ABSTRACT

A method for making a disposable garment with de-elasticed elastic members in the crotch area of the garment is disclosed using means for de-elasticing the elastic members such as macerators, chemicals, selective laser beams, heat, and freezing.

12 Claims, 4 Drawing Sheets

DISPOSABLE GARMENT WITH DE-ELASTICIZED ELASTIC MEMBERS AND METHOD FOR MAKING SAME

This application is a continuation of application Ser. No. 08/269,236, filed Jun. 30, 1994, now abandoned.

BACKGROUND OF THE INVENTION

There are many prior art disposable garments for infants and incontinent adults, including, without limitation, diapers and training pants. In most of such garments, elastic is used to improve the fit of the garment on the wearer, particularly in the leg and waist areas. Such elastic is most often incorporated in such disposable garments by gluing or otherwise fixing homogenous strands of elastic into the disposable garments.

One of the problems with using elastic to improve the fit of disposable garments is properly adjusting the tension of the elastic to maximize fit and comfort. In assembly-line construction of disposable garments, it is not economically feasible to vary the diameter or tensile strength of the elastic if the elastic is a homogeneous strand dispensed from a roll. It is not feasible to adjust the tension of such elastic as it is incorporated into the disposable garment, because to do so would require high speed, precisely coordinated variation in the stretch of the elastic as it is fixed to the disposable garments on the assembly line. Disposable garments often have elastic strands where elastic strands are wholly undesirable, such as the crotch area, because economy and efficiency require that the elastic strands be continuous as they are dispensed along a web on an assembly line. Accordingly, prior disposable garments incorporating elastic often have areas in which the elastic is too tight to maximize the utility of the garment or so tight as to cause undesired discomfort. To avoid such excessive tightness, the elastic may be applied generally to the garment with such little tension that the garment has areas in which the elastic is too loose to maximize the utility of the garment.

For example of excessive tightness, diapers or training pants may have a continuous elastic chord that encircles the garment leg openings and crosses at the crotch area. In such garments, the elastic crossing at the crotch area tends to be of such high tension that the crotch becomes hard and uncomfortable. Such elastic at the crotch area also pulls the edges of the leg openings at the crotch away from the wearer's skin, causing any discharge from the wearer to leak from the garment. Further, such elastic at the crotch area tends to invert the absorbent core at the crotch, causing the core to assume a convex shape from the perspective of the wearer's crotch. Such inversion undesirably causes discharge to run from the surface of the core toward the leg openings of the garment.

To adjust the tension of elastic in disposable garments, the prior art teaches that multiple elastic strands may be used in parallel. To reduce the collective tension of the parallel elastic strands, the distance between the parallel strands may be widened, thus dissipating over a wider area the contractive force of the strands. The foregoing method, however, requires precision orientation of the strands. Further, the foregoing method is of limited effectiveness for varying tension, since the tension can only be dissipated over a widened area, not eliminated.

For the foregoing reasons, it is an object of the present invention to provide a method and apparatus for effectively varying the elastic stress of elastic disposed within a disposable garment. It is a further object of the present invention to reduce the tension of elastic strands crossing at the crotch area of disposable garments.

SUMMARY OF THE INVENTION

To remedy the foregoing problems and to achieve the foregoing objects, there is provided a method Of manufacturing a disposable garment for infants and incontinent adults comprising the steps of applying an adhesive to a surface of a first garment material; stretching an elastic strand; placing the stretched elastic strand on the adhesive of the first garment material; sealingly applying a second garment material to the surface of the first garment material, whereby the stretched elastic strand is sandwiched between the two garment materials; and deactivating the stretched elastic strand in areas where tension is undesirable. For example, the elastic strand may be deactivated by macerators, chemicals, selective laser beams, heat, or freezing means.

Also to achieve the foregoing object there is provided a method of manufacturing a disposable absorbent article for infants and incontinent adults, from a continuous web, comprising the steps of sandwiching at least one stretched elastic member between two garment materials, at least one of the two garment materials comprising a continuous web; applying adhesive means to at least portions of the stretched elastic member, whereby the stretched elastic member is attached to at least one of the two garment materials; deactivating at least portions of the adhered elastic member; cutting the continuous web to the pattern of a disposable absorbent article having a crotch area, two leg openings, and a waist opening; folding the pattern; and sealing the folded pattern to form the disposable absorbent article. For example, the elastic strand may be deactivated by macerators, chemicals, selective laser beams, heat or freezing means.

Also to achieve the foregoing object there is provided a method of manufacturing a disposable absorbent article having a waist opening, two leg openings, and a crotch area, from a continuous web, comprising the steps of adhering at least one stretched elastic member to a continuous web, the web moving relative to a source of the elastic member; deactivating at least a portion of the elastic member; cutting the web to the pattern of disposable absorbent article having a waist opening, two leg openings, and a crotch area; folding the pattern, and sealing the folded pattern to form the disposable absorbent article having a waist opening, two leg openings, and a crotch area. For example, the elastic strand may be deactivated by macerators, chemicals, selective laser beams, or heat. The elastic member may be continuous along at least one edge of each of the two leg openings and transverses the crotch area. The elastic member may be deactivated in the crotch area.

Also to achieve the foregoing object there is provided a disposable absorbent article having a waist opening, two leg openings, and a crotch area, comprising a disposable pant defining a waist opening, two leg openings, and a crotch area; and elastic means adhered to the pant, the elastic means being deactivated at a point of adherence to the pant. The pant may be comprised of a fluid-permeable topsheet and a fluid-impermeable backsheet, and the elastic means may be sandwiched between the topsheet and backsheet. The elastic means it may be continuous along at least one edge of each of the two leg openings.

DETAILED DESCRIPTION OF THE INVENTION AND PREFERRED EMBODIMENT

Figure 1:
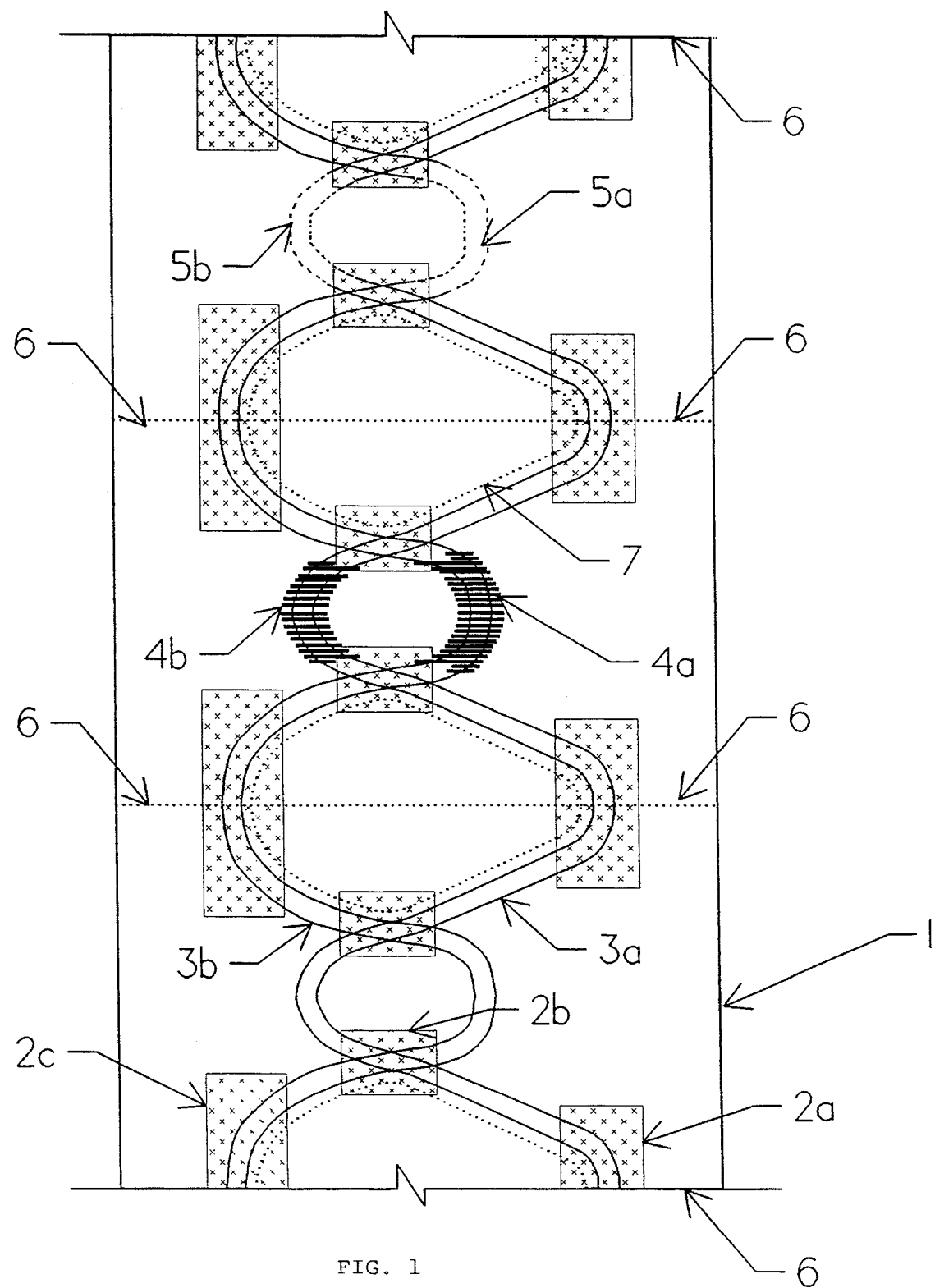
FIG. 1 depicts a top view of a training pant web depicting deactivation of elastic strands in accordance with the present invention.

FIG. 1 depicts an exemplary embodiment of the present invention. Web 1 is a typical, uncut web of non-woven material used in the manufacturing process of training pants. As web 1 is processed through an assembly line, elastic adhesive patches 2a, 2b, and 2c are placed within the layers of web 1 for receiving elastic strands 3a and 3b. The web 1 is fed along an assembly line of rollers. The elastic strands are laid on the adhesive patches 2a, 2b, and 2c by two three-strand elastic-strand weaving mechanisms that traverse the web 1 in accordance with a mechanical program. The elastic strands 2a, 2b, and 2c are pre-tensioned as desired by the mechanical program.

In accordance with the present invention, the elastic strands can be deactivated at points on the web 1 where it is desired to reduce or to eliminate the elastic tension in the finished training-pant product. Deactivation means, such as a mechanical macerator, can cut the elastic strands along pre-determined pathways 4a and 4b, rendered deactivated elastic strands 5a and 5b.

In the embodiment of the invention illustrated in FIG. 1, the web 1 is severed along lines 6 rendering a disposable garment having leg elastic 7, which garment can be folded along a center longitudinal line of the web 1 to render a training pant as is known in the prior art. The crotch of that pant is defined by the area comprising deactivated elastic strands 5a and 5b. Because the elastic strands 5a and 5b are deactivated, they do not cause the crotch of the training pant to be hard, nor do they tend to pull the leg elastic 7 away from the wearer's skin or invert the core.

Figure 2:
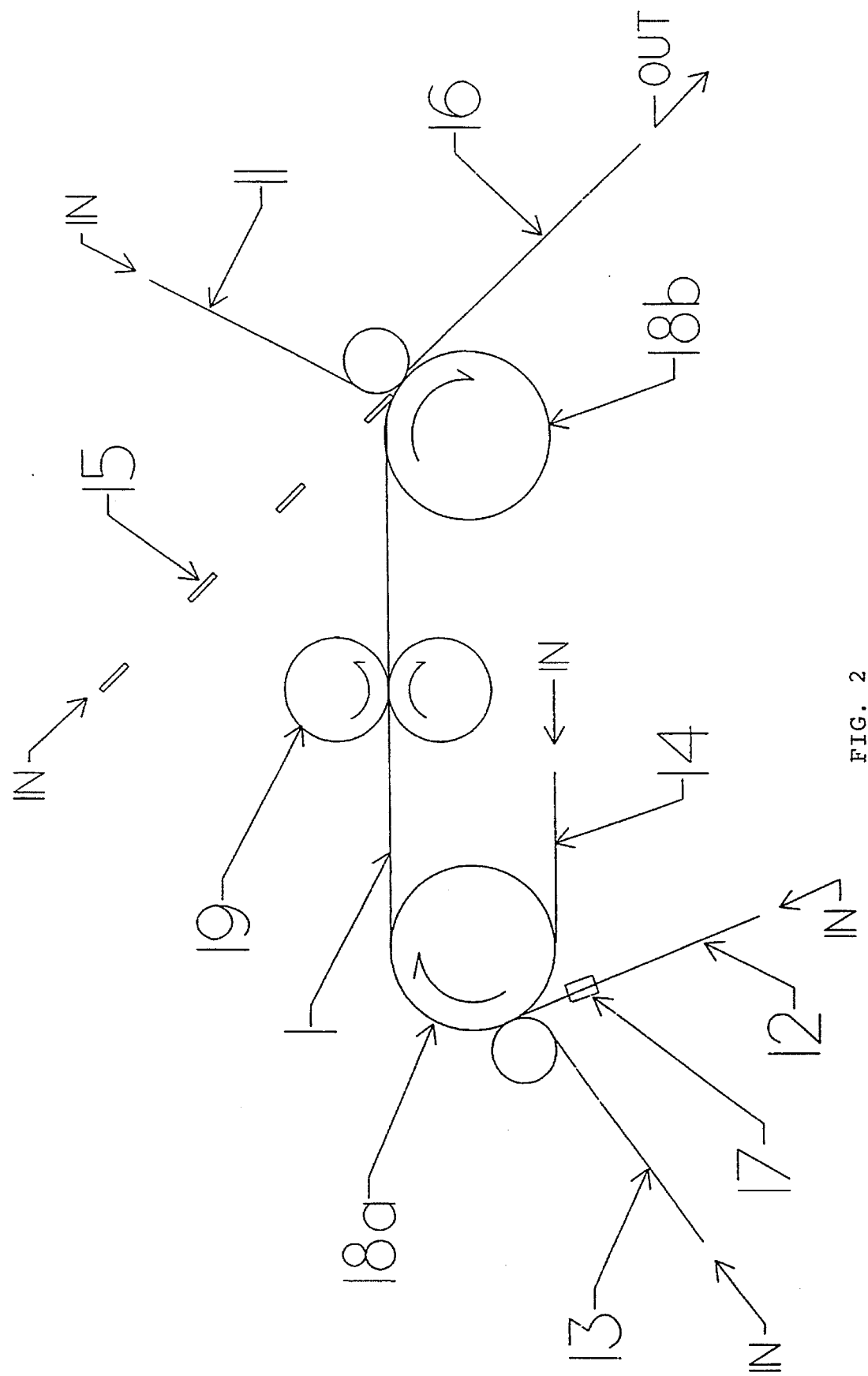
FIG. 2 depicts a side view of an assembly of a disposable garment in accordance with the present invention.

FIG. 2 depicts a typical disposable garment assembly line in operation utilizing the present invention. The web 1 is comprised of an outer non-woven fabric 14 and a film barrier 13. As the outer non-woven fabric 14 rolls over roller 18a, the outer non-woven fabric 14 and the film barrier 13 are pressed together. The point of such pressing together is known in the art as the "nip." At the nip, elastic strands 12 are laid between the outer non-woven fabric 14 at the film barrier 13 by leg elastic weaving mechanisms 17, which laterally traverse the web 1 in accordance with a mechanical program. Adhesive (not shown) may be placed on the outer non-woven fabric 14 before the outer non-woven fabric 14 reaches the nip. As the web 1 rolls over roller 18b, absorbent pads 15 and an inner non-woven liner 11 may be added to the web 1 to form a combined web 16.

Figure 3:
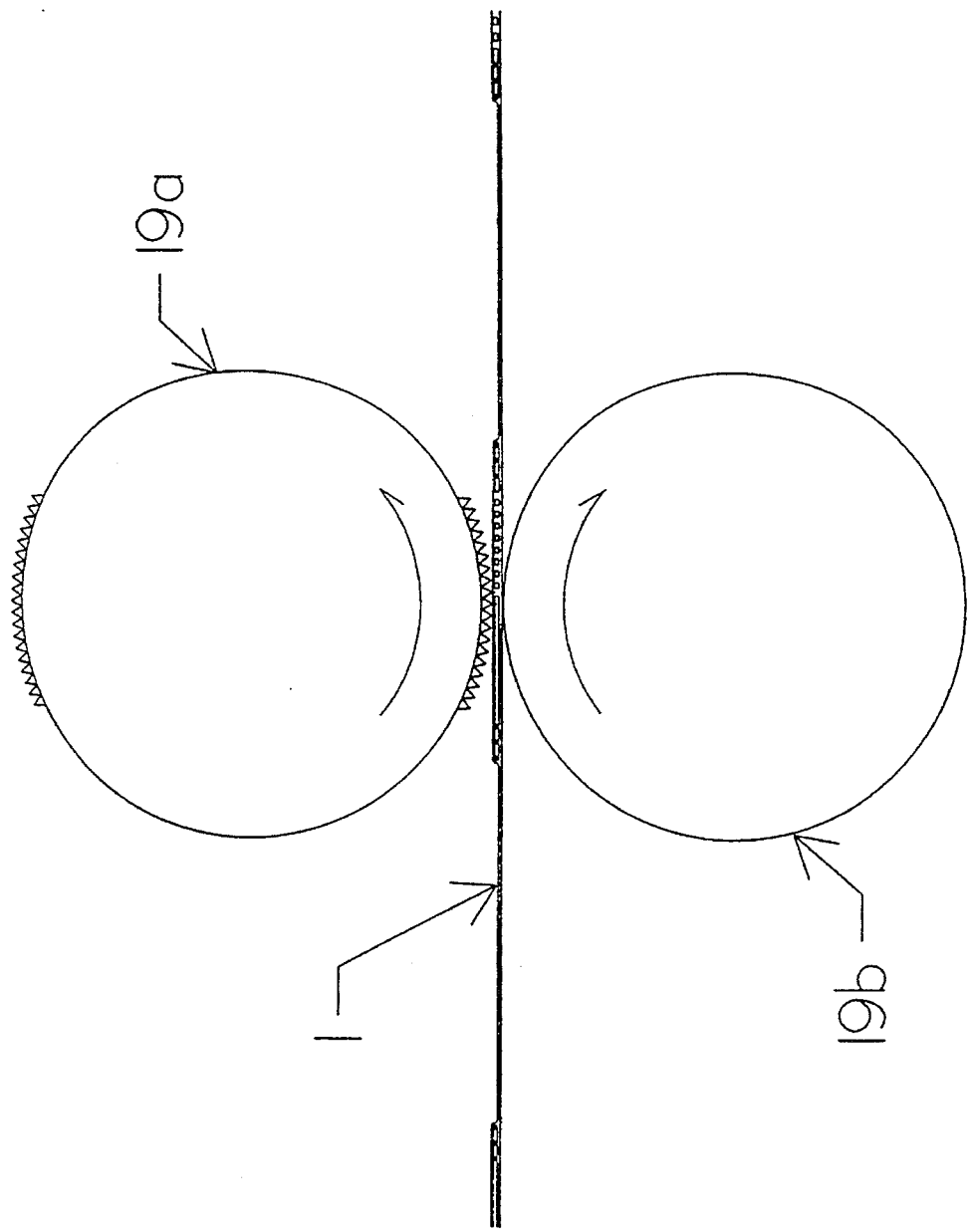
FIG. 3 depicts a side view of an elastic deactivation roller in accordance with the present invention.
Figure 4:
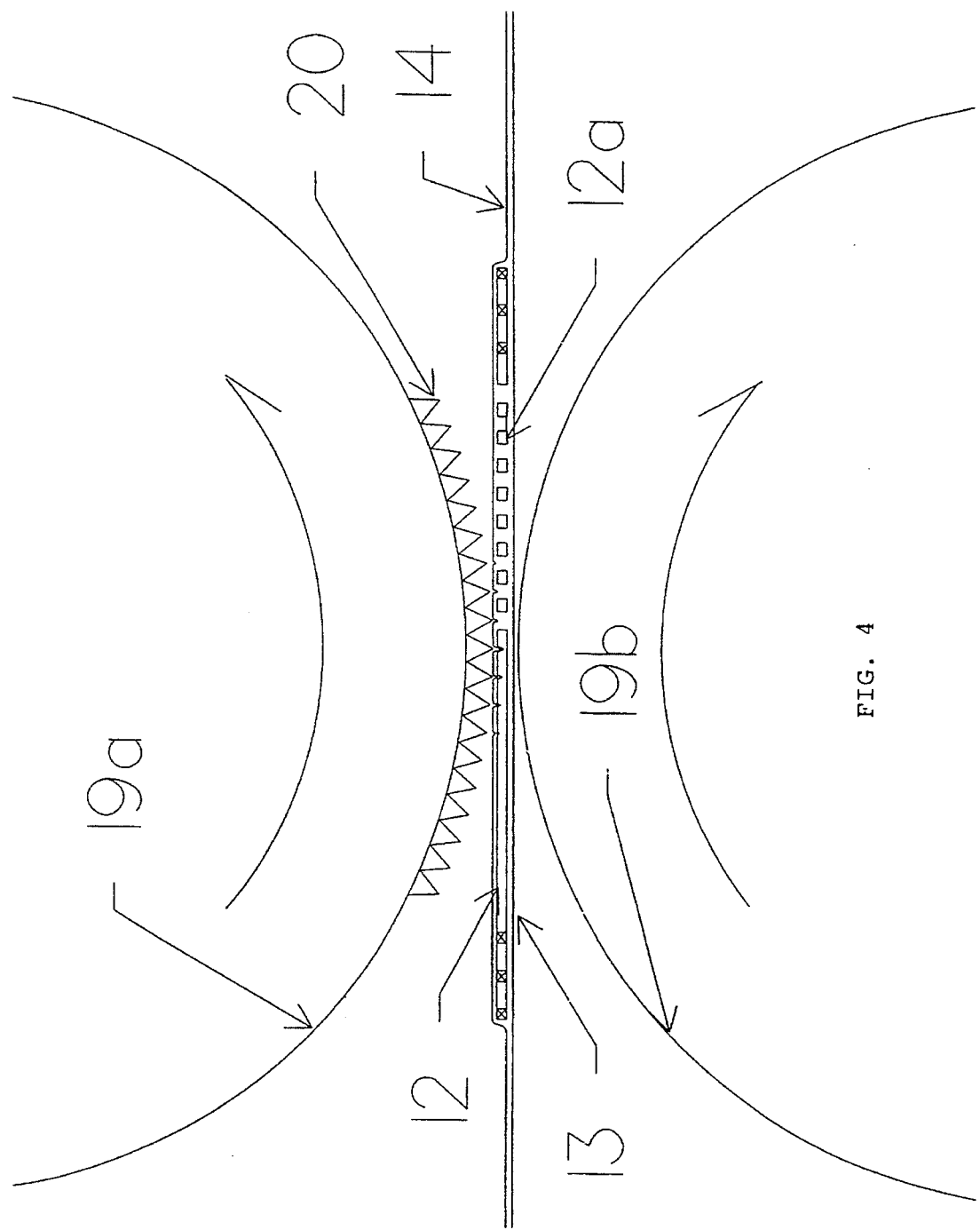
FIG. 4 depicts a close-up side view of the roller depicted in FIG. 3.

As the web 1 rolls between rollers 18a and 18b, macerator 19 works to de-elasticize the elastic strands 12 in accordance with a mechanical program. As illustrated in FIGS. 3 and 4, the web 1 is pressed between macerator rollers 19a and 19b.

As the web 1 is so pressed, teeth 20 of the roller 19a cut in a pre-calculated manner the elastic strands 12, rendering de-elasticized elastic strands 12a.

One skilled in the art will appreciate that various embodiments of the present invention are possible within the scope of the appended claims. In particular, many means may be used to de-elasticize the elastic, including without limitation, mechanical macerators, lasers, heaters, chemicals, and freezing means such as liquid nitrogen. The foregoing means may cut or weaken the elastic. In particular, the freezing means may cause the elastic to crack and to break.

I claim:

1. A method of manufacturing a disposable garment for infants and incontinent adults comprising the steps of:

applying an adhesive to a garment material having first and second leg openings and a crotch area;

stretching an elastic strand along the first leg opening, across the crotch area, and along the second leg opening;

adhering the stretched elastic strand to the garment material; and deactivating the stretched elastic strand in the crotch area of the garment material.

2. The method of claim 1 in which the stretched elastic strand is deactivated by macerating the stretched elastic strand.

3. The method of claim 1 in which the stretched elastic strand is chemically deactivated.

4. The method of claim 1 in which the stretched elastic strand is deactivated by a selective laser beam.

5. The method of claim 1 in which the stretched elastic strand is deactivated by heat.

6. The method of claim 1 in which the stretched elastic strand is deactivated by freezing means.

7. A method of manufacturing from a continuous web a disposable absorbent article having a waist opening, two leg openings, and a crotch area, comprising the steps of:

adhering a stretched elastic member to a continuous web, the web moving relative to a source of the elastic member, the elastic member displaced in a pattern defining a portion of a first leg opening, transversing a crotch area, and defining a portion of a second leg opening;

deactivating a portion of the elastic member transversing the crotch area and;

cutting the web to a pattern of a disposable absorbent article having a waist opening, the two leg openings, and the crotch area.

8. The method of claim 7 in which the stretched elastic strand is deactivated by macerating the stretched elastic strand.

9. The method of claim 7 in which the stretched elastic strand is chemically deactivated.

10. The method of claim 7 in which the stretched elastic strand is deactivated by a selective laser beam.

11. The method of claim 7 in which the stretched elastic strand is deactivated by heat.

12. The method of claim 7 in which the stretched elastic strand is deactivated by freezing means.

* * * * *